United States Patent

Carney et al.

[11] 3,936,467
[45] Feb. 3, 1976

[54] HYDROXYALKYLENIMINO-PHENYL-ACETIC ACIDS

[75] Inventors: Richard William James Carney, New Providence; George de Stevens, Summit, both of N.J.

[73] Assignee: Ciba-Geigy Corporation, Ardsley, N.Y.

[22] Filed: Mar. 25, 1974

[21] Appl. No.: 454,643

Related U.S. Application Data

[63] Continuation-in-part of Ser. No. 307,698, Nov. 17, 1972, , which is a continuation-in-part of Ser. No. 808,343, March 18, 1969, abandoned, which is a continuation-in-part of Ser. No. 790,863, Jan. 13, 1969, abandoned, which is a continuation-in-part of Ser. No. 757,136, Sept. 3, 1968, Pat. No. 3,657,230, which is a continuation-in-part of Ser. No. 716,347, March 27, 1968, abandoned.

[52] U.S. Cl.. 260/293.82; 260/239 BF; 260/293.73; 260/293.75; 260/293.76; 260/293.79; 260/293.81; 260/293.83; 260/293.84; 260/295 R; 260/326.41; 424/244; 424/267; 424/274
[51] Int. Cl.² ........................................ C07D 211/40
[58] Field of Search.... 260/239 BF, 326.41, 293.81, 260/293.82, 293.83, 293.84, 293.73, 293.79, 293.77, 293.75, 293.76

[56] References Cited
UNITED STATES PATENTS

| | | |
|---|---|---|
| 3,669,956 | 6/1972 | Borck et al. ............... 260/293.81 |
| 3,669,973 | 6/1972 | Borck et al. ............... 260/293.81 |
| 3,770,748 | 11/1973 | Borck et al. ............... 260/293.81 |

*Primary Examiner*—Sherman D. Winters
*Attorney, Agent, or Firm*—Joseph G. Kolodny; Theodore O. Groeger; John J. Maitner

[57] ABSTRACT

New α-(cyclic tert. aminophenyl)-aliphatic acids, e.g. those of the formula

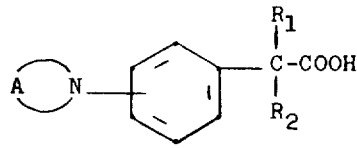

$R_1$ = H or alkyl
$R_2$ = H, alk(en)yl, cycloalk(en)- yl or cycloalk(en)yl-alkyl
A = hydroxylated lower alkylene
and functional derivatives thereof, are anti-inflammatory agents.

5 Claims, No Drawings

HYDROXYALKYLENIMINO-PHENYL-ACETIC ACIDS

CROSS-REFERENCES TO RELATED APPLICATIONS

This is a continuation-in-part of application Ser. No. 307,698, filed Nov. 17, 1972, which in turn is a continuation-in-part of application Ser. No. 808,343, filed Mar. 18, 1969 (now abandoned), which in turn is a continuation-in-part of application Ser. No. 790,863, filed Jan. 13, 1969 (now abandoned), which in turn is a continuation-in-part of application Ser. No. 757,136, filed Sept. 3, 1968 (now U.S. Pat. No. 3,657,230), which in turn is a continuation-in-part of application Ser. No. 716,347, filed Mar. 27, 1968 (now abandoned).

SUMMARY OF THE INVENTION

The present invention concerns and has for its object the provision of new α-(cyclic tert. aminophenyl)-aliphatic acids of the Formula I

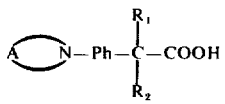

in which $R_1$ is hydrogen or lower alkyl, $R_2$ is hydrogen, lower alkyl, alkenyl, cycloalkyl, cycloalkenyl, cycloalkyl-alkyl or cycloalkenyl-alkyl, Ph is a phenylene radical, and A is free, etherified or esterified mono- or dihydroxy-lower alkylene, of which the oxygen atoms are separated from the nitrogen atom by at least two carbon atoms, of therapeutically acceptable functional acid or amino derivatives thereof, as well as of corresponding pharmaceutical compositions and of methods for the preparation and application of these products, which are useful antiinflammatory agents in the treatment or management of arthritic and dermatopathologic conditions.

DESCRIPTION OF THE PREFERRED EMBODIMENT

The lower alkyl radicals $R_1$ or $R_2$ represent, for example, methyl, ethyl, n- or i-propyl, -butyl, -pentyl, -hexyl or -heptyl. A lower alkenyl radical $R_2$ is, for example, vinyl, allyl, methallyl, 3-butenyl or 1-pentenyl. The term "lower", referred to above and hereinafter in connection with organic radicals or compounds respectively, defines such with up to 7, preferably up to 4, carbon atoms.

A cycloalkyl or cycloalkenyl radical $R_2$ is preferably 3 to 7 ring-membered and unsubstituted or substituted by up to 4 lower alkyls, such as cyclopropyl, 1- or 2-methyl-cyclopropyl, 1,2-, 2,2- or 2,3-dimethyl-cyclopropyl, 1,2,2- or 1,2,3- trimethylcyclopropyl or 2,2,3,3-tetramethyl-cyclopropyl, cyclobutyl, 3,3-dimethylcyclobutyl or 2,2,3-trimethyl-cyclobutyl, cyclopentyl, 2-or 3-methyl-cyclopentyl, 2,5- or 3,4-dimethyl-cyclopentyl, cyclohexyl, 2-, 3- or 4-methyl-cyclohexyl, 2,3-,2,4- or 3,5-dimethylcyclohexyl or 2,4,6-trimethylcyclohexyl or cycloheptyl; 2-cyclopropenyl, 2,3-dimethyl-2-cyclopropenyl, 1-, 2- or 3-cyclopentenyl or -cyclohexenyl, 2- or 3-methyl-2-cyclopentenyl, 3,4-dimethyl-3-cyclopentenyl or 2-, 3- or 4-methyl-1 or 2-cyclohexenyl. A cycloalkyl-lower alkyl or cycloalkenyl-lower alkyl radical $R_2$ is one of the above-mentioned lower alkyl groups, preferably such with up to 4 carbon atoms, having in any position thereof, preferably at the terminal carbon atom, one of said cycloalkyl or cycloalkenyl radicals attached, e.g. cyclopropylmethyl, 2-cyclopentylethyl or 3-cyclopentenylmethyl.

The phenylene radical Ph, carrying the tertiary amino group A⌒N— in the 2-, preferably 3- or especially 4-position, is unsubstituted or substituted in the remaining positions by one or more than one, preferably one or two, of the same or different substituents selected, for example, from lower alkyl, e.g. methyl, ethyl, n- or i-propyl or -butyl, free, etherified or esterified hydroxy or mercapto, such as lower alkoxy or lower alkylmercapto, e.g. methoxy, ethoxy, n- or i-propoxy or -butoxy, methylmercapto or ethylmercapto, or halogeno, e.g. fluoro, chloro, bromo or iodo; trifluoromethyl, nitro, amino, preferably di-lower alkylamino or lower alkanoylamino, e.g. dimethylamino, N-methyl-N-ethylamino, diethylamino, di-n- or i-propylamino or -butylamino; acetylamino or pivaloylamino; furthermore cyano, carbamoyl, di-lower alkylcarbamoyl, carboxy lower alkylsulfonyl, sulfo, sulfamoyl or di-lower alkylsulfamoyl, e.g. N,N-dimethylcarbamoyl or -sulfamoyl, methyl- or ethylsulfonyl. More particularly, the phenylene radical Ph especially represents 1,3- or 1,4-phenylene, but also (lower alkyl)-1,3- or 1,4-phenylene, (lower alkoxy)-1,3- or 1,4-phenylene, mono- or di-(halogeno)-1,3- or 1,4-phenylene, (trifluoromethyl)-1,3- or 1,4-phenylene, (nitro)-1,3- or 1,4-phenylene, (amino)-1,3-or 1,4-phenylene or (di-lower alkylamino)-1,3- or 1,4-phenylene.

The cyclic tertiary amino group A⌒N— is, for example, monocyclic lower alkyleneimino, e.g. pyrrolidino, piperidino, 1,4-pentyleneimino, 2,5- or 1,6-hexyleneimino, 2,6- or 1,7-heptyleneimino, which is substituted by one or two free, etherified or esterified hydroxy groups, such as lower alkoxy or alkanoyloxy, e.g. methoxy, ethoxy, n- or i-propoxy or -butoxy; acetoxy, propionyloxy, butyryloxy or pivalyloxy groups, separated from the nitrogen by at least two carbons.

Therapeutioally acceptable functional derivatives of the acids of Formula I are preferably their esters, for example, their lower alkyl, lower alkenyl, 3 to 7 ring-membered cycloalkyl, cycloalkenyl, cycloalkyl-lower alkyl or cycloalkenyl-lower alkyl, aryl or aralkyl esters, e.g. the HPh or HPh-lower alkyl esters, free or etherified hydroxy-lower alkyl, e.g. lower alkoxy- or 3 to 7 ring-membered cycloalkoxy-lower alkyl or tert. amino-lower alkyl esters, of which the esterifying moiety has been exemplified above and if it contains hetero atoms, these are separated from each other and the carboxy oxygen by at least 2, preferably 2 or 3 carbon atoms. A tertiary amino group therein is, for example, di-lower alkylamino or lower alkyleneimino, e.g. dimethylamino, diethylamino, pyrrolidino or piperidino, or monoaza-, monooxa- or monothia-lower alkyleneimino, such as piperazino, 4-lower alkyl-piperazino, e.g. 4-(methyl or ethyl)-piperazino, morpholino or thiamorpholino. Other functional derivatives of the acids of Formula I are, for example, unsubstituted or substituted amides or thioamides, e.g. mono- or di-lower alkylamides, HPh-amides, HPh-lower alkylamides, monocyclic lower alkyleneamides, monoaza-, monooxa- or monothia- lower alkyleneamides, furthermore the corresponding thioamides, hydroxamic acids, nitriles, ammonium or metal salts. Amino derivatives are the N-oxide, lower alkyl- or HPh-lower alkyl quaternaries and acid addition salts.

The compounds of the invention possess valuable pharmacological properties. Besides analgesic and antifungal activity, they exhibit anti-inflammatory effects, as can be demonstrated in in vitro or animal tests, using for the latter advantageously mammals, such as mice, rats or guinea pigs as test objects. The former tests can be performed according to the gradient plate method with fungi selected, for example, from Trichophyton, Microsporum or Epidermophyton, e.g. *T. mentagrophytes, T. rubrum* or *T. sinii; M. canis* or *M. gypseum;* or *E. floccosum.* The antifungal activity can also be observed in vivo, e.g. according to Molinas, J. Investig. Dermatol. 25, 33(1955), where guinea pigs are infected on the shaven back with a homogenous agar suspension of a 10 day old culture of *T. mentagrophytes* grown on Sabouraud's agar. Treatment with 0.5–2% medicated solutions or ointments is started after 24 hours and continued once daily for 10 days. During this time, portions of hair and skin skales are taken from 5 different sites of the infected area and subcultured on Mycosel agar plates, which are incubated and examined for growth. The analgesic effects can be demonstrated, for example, according to the mouse writhing test, described inter alia by Siegmund et al. Proc. Soc. Exp. Biol. & Med. 95, 729 (1957) at oral doses between about 50 and 200 mg/kg/day. Anti-inflammatory activity can be shown, for example, according to Winter et al, Proc. Soc. Exp. Biol. & Med. 111, 544 (1962). There, the compounds of the invention are applied, in the form of aqueous solutions or suspensions, which may contain carboxymethyl-cellulose or polyethylene glycol as solubilizers, by stomach tube to male and female mature rats, in the dosage range between about 0.1 and 75 mg/kg/day, preferably between about 0.5 and 50 mg/kg/day, advantageously between about 1 and 25 mg/kg/day. About 1 hour later 0.06 ml of a 1% aqueous saline suspension of carrageenin is injected into the rat's left hind paw and 3–4 hours subsequently any anti-inflammatory activity can be expressed by the difference of the volume and/or weight of the edematous left paw and that of the right paw, as compared with said difference estimated from untreated control animals. According to the adjuvant arthritis test, male rats are sensitized with 0.05 ml of said 1% carrageenin suspension, applied under ether anesthesia to all four paws. After 24 hours 0.1 ml of a 1% suspension of M. butyricum in mineral oil is injected intradermally into the tail and 7 days later the compounds of the invention are applied as shown above for a 14 day period. The rats are weighed once weekly and the secondary arthritic lesions scored 3 times a week as to number and severity. The results obtained are compared with those of untreated arthritic rats. In view of the test results obtained, the compounds of the invention are useful analgesic, antifungal and especially antiinflammatory agents in the treatment or management of arthritic and dermatopathologic conditions. They are also useful intermediates in the preparation of other valuable products, preferably of pharmacologically active compounds.

Preferred compounds of the invention are those of Formula I in which:

a. $R_1$ is hydrogen or lower alkyl, $R_2$ is hydrogen, lower alkyl or lower alkenyl, Ph is unsubstituted phenylene or phenylene substituted by one or two members selected from the group consisting of lower alkyl, hydroxy, mercapto, lower alkoxy, lower alkyl-mercapto, halogeno, trifluoromethyl, nitro, amino, di-lower alkylamino, lower alkanoylamino, cyano, carbamoyl, di-lower alkyl-carbamoyl, carboxy, lower alkylsulfonyl, sulfo, sulfamoyl or di-lower alkyl-sulfamoyl and A is alkylene, substituted by one or two members selected from hydroxy, lower alkoxy or lower alkanoyloxy separated from the nitrogen by at least 2 carbons;

b. $R_1$, Ph and A⌒N— have the meaning given under item (a) and $R_2$ is 3 to 7 ring-membered cycloalkyl, cycloalkenyl, cycloalkyl- lower alkyl or cycloalkenyl-lower alkyl, or a lower alkyl ester, lower alkenyl ester, 3 to 7 ring-membered cycloalkyl ester, cycloalkenyl ester, cycloalkyl-lower alkyl ester, cycloalkenyl- lower alkyl ester, HPh-ester, HPh-lower alkyl ester, hydroxy- lower alkyl ester, lower alkoxy-lower alkyl ester, di-lower alkylamino-lower alkyl ester, lower alkyleneimino-lower alkyl ester, monoaza-, -oxa- or -thia-lower alkyleneimino-lower alkyl ester or A⌒N—lower alkyl ester in which esters 2 hetero atoms are separated from each other by at least 2 carbon atoms, the amide, thioamide, a mono- or di-lower alkylamide, mono- or di-lower alkyl-thioamide, lower alkyleneamide, lower alkylenethioamide, HPh-amide, HPh-thioamide, HPh-lower alkylamide, HPh-lower alkylthioamide, morpholide, thiamorpholide or hydroxamic acid, the N-oxide, a lower alkyl quaternary, HPh-lower alkyl quaternary or a therapeutically useful salt of the compounds listed under items (a) or (b).

Particularly useful are the compounds of Formula I, in which:

c. $R_1$ is hydrogen, $R_2$ is hydrogen or lower alkyl, Ph is 1,3- or 1,4-phenylene, (lower alkyl)-1,3- or 1,4-phenylene, (lower alkoxy)-1,3- or 1,4-phenylene, (lower alkylmercapto)-1,3- or 1,4-phenylene, mono- or di-(halogeno)-1,3- or 1,4-phenylene, (trifluoromethyl)-1,3- or 1,4-phenylene, (nitro)-1,3- or 1,4phenylene, (amino)-1,3- or 1,4-phenylene or (di-lower alkylamino)-1,3- or 1,4-phenylene, the group A⌒N— is mono- or di-(hydroxy- or lower alkanoyloxy)-alkyleneimino, wherein the oxygen atom is separated from the nitrogen atom by at least two carbon atoms, $R_1$, Ph and A⌒N— have the meaning given under item (c) and $R_2$ is 3 to 7 ring-membered cycloalkyl or cycloalkyl-lower alkyl, or a lower alkyl ester, the amide, a mono- or di-lower alkylamide, the N-oxide, an alkali metal or alkaline earth metal salt or a therapeutically useful acid addition salt of the compounds listed under items (c) and (d).

Outstanding compounds of the invention are those of Formula II

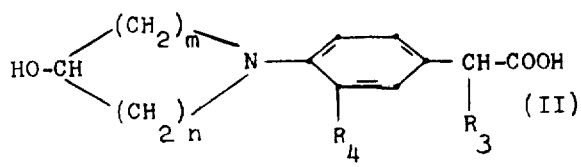

in which:

e. $R_3$ is hydrogen or alkyl with up to 4 carbon atoms, $R_4$ is hydrogen, alkyl or alkoxy with up to 4 carbon atoms, halogeno or trifluoromethyl, each of $n$ and $m$ is an integer from 1 to 3 and the sum $m + n$ is 3 to 6 or f. $R_4$, $m$ and $n$ have the meaning given under item (e) and $R_3$ is 3 to 4 ring-membered lower cycloalkyl or cycloalkylmethyl, or the methyl, ethyl, n- or i-propyl or -butyl ester, the sodium or potassium salt or a therapeutically useful acid addition salt of the compounds listed under items (e) and (f).

Especially valuable are compounds of the Formula II, in which:

g. $R_3$ is hydrogen, methyl or ethyl and $R_4$ is hydrogen or chloro, $m$ is the integer 1 or 2, $n$ is the integer 2 or 3 and $m + n$ is 4, h. $R_4$, $m$ and $n$ have the meaning given under item (g) and $R_3$ is cyclopropyl or cyclopropylmethyl; or the methyl or ethyl ester, the sodium or potassium salt or a therapeutically useful acid addition salt of the compounds listed under items (g) and (h).

The most preferred embodiments of the present invention are the compounds of Formula II, wherein:

i. $R_3$ is hydrogen or methyl, $R_4$ is hydrogen or chloro, $m = 1$, $n = 3$.

j. $R_3$ is hydrogen or methyl, $R_4$ is hydrogen or chloro, $m = 2$, $n = 2$; or the methyl or ethyl ester, the sodium or potassium salt or a therapeutically useful acid addition salt of the compounds listed under items (i) and (j).

The compounds of this invention are prepared according to methods known per se. For example, they are obtained by:

a. converting in a compound of the Formula III

(III)

in which $X_1$ is a substituent capable of being converted into the free or functionally converted

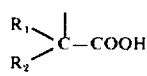

moiety, $X_1$ into said acid group or b. converting in a compound of Formula IV

(IV)

or a functional derivative thereof, in which $X_2$ is a substituent capable of being converted into A N—, $X_2$ into said cyclic tert. amino group and, if desired, converting any resulting compound into another compound of the invention.

According to process (a), the compounds of the invention are prepared either by ($\alpha$) introduction of the whole free or functionally converted acid moiety

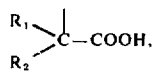

or any part thereof (preferably the carboxylic function), into compounds of Formula III, or by $\beta$) liberation of said acid moiety from a suitable group containing already the required number of carbon atoms, i.e. the liberation of a potential carboxy or alkylidene moiety.

Accordingly, the simplest substituent $X_1$ is a hydrogen atom, a metallic group or a reactively esterified hydroxy group. The former is, for example, an alkali metal, e.g. a lithium atom, or a substituted alkaline earth metal, zinc or cadmium atom, such as halomagnesium or lower alkyl zinc or cadmium, e.g. chloro-, bromo- or iodomagnesium, methyl or ethyl zinc or cadmium. A reactively esterified hydroxy group is preferably such derived from a strong mineral or sulfonic acid, such as a hydrohalic, sulfuric, lower alkane or benzene sulfonic acid, e.g. hydrochloric, hydrobromic, methane-, ethane-, benzene- or p-toluenesulfonic acid. The corresponding starting material of Formula III is reacted with the acid having the formula

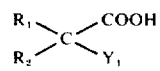

or a suitable derivative, e.g. a corresponding salt, ester, amide or nitrile thereof, in which formulae one of $X_1$ and $Y_1$ is the above-described metallic group and the other said reactively esterified hydroxy group, or $X_1$ is hydrogen and $Y_1$ is a free or reactively esterified hydroxy group. Such reaction is performed according to the classical Grignard or Friedel-Crafts syntheses, in which a new carbon-carbon bond is formed from separate reactants. The latter synthesis is performed in the presence of a Lewis acid, such as an aluminum, boron, antimony V, ferric or zinc salt, e.g. the chlorides thereof, or hydrofluoric, sulfuric or preferably polyphosphoric acid, which latter agent is advantageously used with the above glycolic acids or their derivatives, i.e. those in which $Y_1$ is hydroxy. In case $X_1$ is a hydrogen atom and Ph contains a free or functionally converted $\gamma$-carboxy-2-alkenyloxy group in the ortho or para position thereto, such allyl ether starting material, e.g. that of the formula A N—Ph—O—CH$_2$—CH=CH—COOR$_1$, can be rearranged according to the Claisen (Cope) rearrangement procedure, for example, by heating it up to about 300° or less, to yield compounds of Formula I in which $R_2$ is lower alkenyl and Ph contains a hydroxy group ortho or para to the acid moiety, or functional acid derivatives, e.g. esters or lactones, thereof.

The substituent $X_1$ in Formula III is also the group

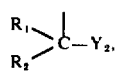

in which $Y_2$ is a metallic group, e.g. such mentioned above, an ammonium group, such as tri-lower alkylammonium or di-lower alkyl-aralkylammonium, e.g. trimethylammonium or dimethylbenzylammonium, or a free or reactively converted, such as esterified, etherified or salified, hydroxy group, e.g. such esterified as mentioned above, or etherified with a lower alkanol or aralkanol, or salified with an alkali or alkaline earth metal, e.g. sodium, potassium or calcium. Such metal compound, ester, ether or alcoholate of Formula III is reacted with a reactive derivative of carbonic or formic acid, whereby both reactants at most contain one metal atom. The metal or Grignard compound can be reacted with any suitable, metal free carbonic or formic acid derivative, advantageously carbon dioxide or disulfide, but also a corresponding carbonate or haloformate, e.g. diethyl carbonate or thiocarbonate; ethyl or propyl orthocarbonate; ethyl, tert. butyl, allyl, 2-methoxyethyl, 3-chloropropyl, phenyl or benzyl chloroformate; cyanogen or carbamoyl halides, e.g. cyanogen bromide or diethylcarbamoyl chloride. The starting material, in which $Y_2$ is an ammonium or free or reactively converted hydroxy group, is advantageously reacted with a metal cyanide, e.g. sodium or potassium cyanide, and that in which $Y_2$ is free, esterified or salified hydroxy, or the dehydrated unsaturated derivative thereof (wherein $X_1$ is a corresponding 1-alkenyl group) can also be reacted with carbon monoxide. The latter may be applied under neutral, basic or acidic conditions respectively, e.g. in the presence of sulfuric acid, under high pressure and/or temperature, e.g. up to 400° at and 300°, advantageously in the presence of heavy metal catalysts, e.g. nickel or cobalt salts or carbonyl derivatives thereof. The carbon monoxide may also be generated from appropriate sources, such as formic acid and high boiling mineral acids, e.g. sulfuric or phosphoric acid.

Another substituent $X_1$ is the group

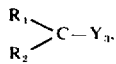

wherein $Y_3$ is a substituent convertible into a free or functionally converted carboxy group. The conversion of $Y_3$ into the latter group can be performed either by oxidation or rearrangement. In the former case $Y_3$ is, for example, methyl, hydroxymethyl, borylmethyl, hydroxyiminomethyl, formyl, lower 1-alkenyl or 1-alkynyl, lower 1,2-dihydroxyalkyl or acyl, such as lower alkanoyl, alkenoyl, free or esterified carboxycarbonyl. In the corresponding starting material of Formula III, containing said potential carboxy function, $Y_3$ is transformed into free or functionally converted carboxy according to standard oxidation methods, for example, with the use of air or pure oxygen, preferably in the presence of catalysts, such as silver, manganese, iron or cobalt catalysts, or with oxidation agents, e.g. hydrogen peroxide or nitric oxides, oxidizing acids or their salts, such as hypohalous, periodic, nitric or percarboxylic acids or suitable salts thereof, e.g. sodium hypochlorite or periodate, peracetic, perbenzoic or monoperphthalic acid, heavy metal salts or oxides, such as alkali metal chromates or permanganates; chromic or cupric salts, e.g. halides or sulfates thereof, or silver, mercuric, vanadium V, chromium VI or manganese IV oxide, in acidic or alkaline media respectively. In said oxidations, for which starting materials are chosen, in which A⃝N- is less sensitive to oxidation than $Y_3$, e.g. aromatic bicyclic alkenyleneimino, usually the free carboxylic acids of Formula I, or salts thereof, are obtained. However, by subjecting, for example, a hydroxyiminomethyl compound (oxime) to Beckmann rearrangement, e.g. treatment with sulfuric acid, p-toluenesulfonyl chloride or phosphorus pentachloride, or to oxidation, e.g. with hydrogen peroxide or any of said percarboxylic acids, or reacting the corresponding formyl or acyl compound (aldehyde or ketone) with hydrazoic acid according to the Schmidt reaction, e.g. in the presence of sulfuric acid, or the aldehyde with a sulfonyl- or nitro-hydroxamate, a nitrile, amide or hydroxamic acid will be formed respectively. A starting material in which $Y_3$ is free or esterified carboxycarbonyl, e.g. lower carbalkoxycarbonyl, can be converted into the acid of Formula I either by oxidation, e.g. with hydrogen peroxide in acidic media, such as mineral acids, or by decarbonylation, which preferably is carried out by pyrolysis, advantageously in the presence of copper or glass powder.

Finally, the substituent $X_1$ in Formula III may be such a moiety, which primarily is capable of liberating the required alkylidene group

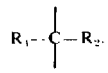

Such moiety is, for example, the free or functionally converted group

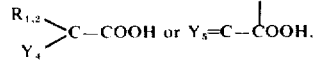

wherein each of $Y_4$ or $Y_5$ are convertible into $R_1$ and/or $R_2$ respectively, for example, by reduction, decarboxylation, deacylation or desulfurization. For example, $Y_4$ is a free or reactively esterified or etherified hydroxy or mercapto group as mentioned above, e.g. hydroxy, mercapto, chloro, bromo, iodo, benzyloxy or benzylmercapto and $Y_5$ a lower alkylidene, cycloalkylidene, cycloalkyl-alkylidene, oxo or thiono group. The corresponding starting material, or the quaternary o- or p-quinonmethides thereof, obtainable by splitting off $Y_4H$ from said compounds of Formula III, in which at least one of $R_1$ and $R_2$ is hydrogen, e.g. with the use of strong mineral acids or alkalis, can be reduced either with catalytically activated or nascent hydrogen, such as hydrogen in the presence of nickel, palladium or platinum catalysts, or with hydrogen generated by electrolysis or the action of metals on acids, alkalis or alcohols, such as zinc, amalgamated zinc, iron or tin on aqueous mineral or carboxylic acids, e.g. hydrochloric or acetic acid, zinc or aluminum-nickel alloys on aqueous alkali metal hydroxides, or sodium, potassium or their amalgams on lower alkanols. Also reducing and/or desulfurizing agents may be applied, depending on the starting material chosen. In case $Y_4$ is hydroxy, the reducing agent may be an aqueous suspension of phosphorus and iodine, hydriodic acid, stannous chloride or sodium sulfite or dithionite, or in case $Y_4$ is esterified hydroxy, e.g. halogeno, an aliphatic or cycloaliphatic metal compound, e.g. a corresponding $R_1$ or $R_2$ lithium or Grignard compound may be used as reducing agent. The latter metal compounds may also be applied in the reduction of said quinonmethides. In case $Y_5$ is oxo, the Clemmensen, Wolff-Kishner or Huang-Minlon procedures may be applied, wherein nascent hydrogen or hydrazine are used, the latter advantageously in the presence of strong alkalis, e.g. high boiling aqueous or glycolic sodium or potassium hydroxide solutions. In the reduction of mercapto, free or ketalized thiono compounds, desulfurization agents are advantageously applied, such as mercury or copper oxide or Raney nickel. In case $Y_4$ represents carboxy, the corresponding malonic acid derivative is decarboxylated by pyrolysis, advantageously in acidic media, or $Y_4$ stands for another acyl radical, such as lower alkanoyl or aralkanoyl, e.g. acetyl or benzoyl, the $\beta$-keto acid is subjected to acid splitting by the action of strong alkalis, e.g. those mentioned above.

Another substituent $X_1$, also providing said alkylidene group, is an unsubstituted or substituted acetyl group, e.g. $—CO—(CN_2)—R_2$ or $CO—(CR_1,R_2)$-halogen. The corresponding unsubstituted acetyl starting material is converted into the compounds of the invention according to the Willgerodt-Kindler reaction, e.g. by the action of sulfur in the presence of ammonia, primary or secondary amines and advantageously of sulfonic acids, e.g. p-toluenesulfonic acid, and said substituted acetyl compounds according to the Wolff (Arndt-Eistert) reaction, e.g. by hydrolysis, alcoholysis, ammonolysis or aminolysis of corresponding $\alpha$-diazo-ketones, advantageously while irradiated or heated in the presence of copper or silver catalysts, or according to the Favorskii (Wallach) reaction respectively, e.g. by the action of strong alkalis or soluble silver salts, such as silver nitrate, on corresponding $\alpha$-haloketones.

According to process (b), the cyclic tertiary amino group A⌒N— is either (a) introduced into the phenylene moiety Ph, or (b) a primary, secondary, acyclic (open) or unsaturated cyclic tertiary amino group, present therein, converted into the desired hydroxylated cyclic tertiary amino group. Accordingly, $X_2$ is, for example, a hydrogen atom, a metallic group or a free or reactively esterified hydroxy group, e.g. those groups shown above, preferably an alkali metal or halogen atom respectively. The corresponding starting material of Formula IV is reacted with the compound A⌒N—$Y_1$, in which one of $X_2$ and $Y_1$ is hydrogen or said metallic group, e.g. lithium or sodium, and the other said free or reactively esterified hydroxy group, e.g. fluorine or chlorine. In case $X_2$ is hydrogen and $Y_1$ halogen, the reaction is carried out analogous to the Friedel-Crafts syntheses mentioned above, i.e. in the presence of Lewis acids or, in case $Y_1$ is hydroxy, in the presence of alkalis, e.g. potassium hydroxide. In case $X_2$ is hydroxy or lower alkanoyloxy, the reaction is advantageously carried out in the presence of a dehydration or dehydrogenation catalyst, such as a mineral acid or a salt thereof, e.g. hydrochloric acid, ammonium sulfite or sodium bisulfite, activated aluminum oxide, Raney nickel or palladium-charcoal.

The conversion of any primary, secondary, acyclic or unsaturated cyclic tertiary amino group $X_2$ into A⌒N— can simply be performed by transamination with the amine A⌒N—H. The latter is advantageously used in excess and in the presence or absence of catalysts, e.g. the above-mentioned dehydration or dehydrogenation catalysts, and elevated temperature and/or pressure. A starting material of Formula IV, in which $X_2$ is primary amino, can also be reacted with the glycol HO—A—OH, or advantageously a reactive functional derivative thereof, such as an ester, cyclic ether or the dehydrated unsaturated (olefinic) derivative or corresponding aldehyde of said glycol, preferably a halide thereof, e.g. such mentioned above. These condensations are advantageously carried out in the presence of water or acid binding agents, such as alkali metals, their alcoholates or carbonates and the addition of the unsaturated compounds to the amino group preferably in the presence of catalysts, e.g. copper, cobalt or molybdenum catalysts, and/or acids or bases. A mono-hydroxylated A⌒N— group can be subjected to dehydration, to form the corresponding unsaturated group, or reactive derivatives thereof, such as a reactive ether or ester of the hydroxy compounds, or an acyl derivative of the nitrogen bases, e.g. a tert. butyl ether or a tosylate, brosylate or xanthate respectively, may analogously be split. Dehydration is preferably carried out with the use of concentrated mineral or sulfonic acids, Lewis acids or carboxylic acid anhydrides, e.g. hydrobromic, sulfuric, phosphoric or p-toluenesulfonic acid or acetic anhydride. Preferably reactive esters of the hydroxy compounds are pyrolyzed, advantageously under reduced pressure. The resulting compounds, wherein $X_2$ is olefinic alkenyleneimino, can be epoxidized therein in the usual manner, e.g. with the use of aliphatic or aromatic percarboxylic acids, e.g. peracetic or perbenzoic acid. The resulting epoxides are converted into compounds of Formula 1 wherein A⌒N is dihydroxylated alkyleneimino, by treatment with either aqueous acids or bases, e.g. mineral acids or alkali metal hydroxides.

Finally the compounds of the invention can be obtained by reduction of compounds of Formula IV, wherein $X_2$ is mono- or dioxoalkyleneimino. Said reduction is preferably carried out with the use of simple or complex borohydrides, e.g. sodium borohydride, if desired in the presence of catalysts, e.g. aluminum chloride. Said reduction can also be performed with lower alkyl Grignard compounds, e.g. lower alkylmagnesium bromides, to yield compounds of Formula I, wherein A⌒N is branched hydroxyalkyleneimino.

The compounds of the invention so obtained can be converted into each other according to methods known per se. For example, resulting free acids may be esterified with the corresponding alcohols in the presence of a strong acid, e.g. hydrochloric, sulfuric, benzene or p-toluene sulfonic acid, or with diazo compounds, or converted into their halides by treatment with thionyl halides or phosphorus halides or oxyhalides. Resulting esters may be hydrolyzed or transesterified in the presence of acidic or alkaline agents, e.g. mineral or complex heavy metal acids or alkali metal carbonates or alcoholates, or treated with ammonia or corresponding amines. Resulting acid halides may be treated with alcohols, ammonia or amines in order to obtain the corresponding esters or amides respectively. Resulting amides or thioamides (Willgerodt) can be hydrolyzed under acidic or alkaline condition, e.g. with the use of aqueous mineral and/or carboxylic acids or alkali metal hydroxides, also alcoholyzed, transaminated or desulfurized, e.g. with the use of mercuric oxide or alkyl halides followed by hydrolysis. Resulting nitriles likewise can be hydrolyzed or alcoholyzed, e.g. with the use of concentrated aqueous or alcoholic acids or alkalis or also with alkaline hydrogen peroxide. A resulting ester, salt or nitrile, containing in $\alpha$-position at least one hydrogen atom, can be metallized therein, e.g. with the use of alkali metals or their derivatives, such as phenyl lithium, triphenylmethylsodium or sodium hydride, amides or alcoholates, and thereupon reacted with reactive esters of $R_1$—OH and/or $R_2$—OH. Resulting compounds may also be halogenated in the Ph-moiety, e.g. with the use of halogens, which are advantageously applied in the presence of Lewis acids, e.g. ferric, aluminum, antimony III or tin IV halides, or with the use of halogenation agents, e.g. hydrochloric acid and hydrogen peroxide or sodium chlorate, nitrosyl chloride or bromide, bromosuccin- or phthalimide. Furthermore, nitration may be applied to final products, advantageously with the use of nitric acid or nitrates under acidic conditions, e.g. in the presence of sulfuric or trifluoroacetic acid respectively. Resulting nitro compounds may be reduced, for example, with catalytically activated or nascent hydrogen and, if desired, the primary amino compounds obtained, either treated with reactive esters of corresponding alcohols or glycols, or with reactive functional acid derivatives, in order to obtain secondary, tertiary, quaternary or acylated amino compounds respectively. Said primary amines can also be treated with nitrous acid, to yield diazonium salts, which can be converted according to the Sandmeyer reaction into the corresponding hydroxy, halogeno, cyano, alkoxy or alkylmercapto compounds, e.g. by hydrolyzing the diazonium salt at elevated temperatures, or reacting it with cuprous halides or cyanide, or with a lower alkanol or alkylmercaptane respectively, preferably under neutral or slightly acidic or alkaline conditions. In resulting phenolic products, the hydroxy or mercapto group can be etherified, e.g. by reacting the corresponding alkali metal phenolates with lower alkyl halides or sulfonates, or resulting phenol ethers are hydrolyzed, e.g. with the use of strong acids or acidic salts, e.g. hydrobromic and acetic acid or pyridine hydrochloride. In the above reduction, care should be taken or starting materials and final products properly selected, in order to retain free, etherified or esterified hydroxylation in $A\bigcirc N-$.

A resulting acid can be converted into its salts according to conventional methods, for example, by reacting it with an about stoichiometric amount of a suitable salt-forming reagent, such as ammonia, an amine or an alkali or alkaline earth metal hydroxide, carbonate or hydrogen carbonate. A salt of this type can be reconverted into the free acid by treatment with an acid, e.g. hydrochloric, sulfuric or acetic acid, until the proper pH has been reached. A resulting basic compound can be converted into a corresponding acid addition salt, for example by reacting it with an inorganic or organic acid, such as a therapeutically useful acid, or with a corresponding anion exchange preparation, and isolating the desired salt. An acid addition salt may be converted into the free compound by treatment with a base, e.g. a metal hydroxide, ammonia or a hydroxyl ion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicylic, aminosalicylic, embonic, nicotinic, methanesulfonic, ethanesulfonic, hydroxy-ethanesulfonic, ethylenesulfonic, benzenesulfonic, halogenbenzenesulfonic, toluenesulfonic, naphthalenesulfonic and sulfanilic acid; methionine, tryptophan, lysine and arginine.

These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

Resulting mixtures of isomers can be separated into the single isomers by methods in themselves known, e.g. by fractional distillation, crystallization and/or chromatography. Racemic products can likewise be resolved into the optical antipodes, for example by separation of diastereomeric salts thereof, e.g. by the fractional crystallization of d- or l-tartrates or d-α-(1-naphthyl)ethylamine or l-cinchonidine salts.

The above reactions are carried out according to standard methods, in the presence or absence of diluents, preferably such as are inert to the reagents and are solvents thereof, of catalysts, condensing or neutralizing agents and/or inert atmospheres, at low temperatures, room temperature or elevated temperatures, at atmospheric or superatmospheric pressure.

The invention also comprises any modification of the above process, wherein a compound resulting as an intermediate at any stage thereof, is used as starting material and the remaining steps are carried out, or the process is discontinued at any stage thereof, or in which the starting material is formed under the reaction conditions or is used in the form of its salts or reactive derivatives. For example, in most of the above-described oxidation methods, wherein $Y_3$ is converted into a free or functionally converted carboxy group, the corresponding aldehydes ($Y_3$ is formyl) are formed intermediarily. According to the haloform reaction ($Y_3$ is acetyl) intermediarily formed trihaloketones are hydrolyzed under the applied alkaline conditions, to yield the corresponding salts or esters of the acids of Formula I. Also, the quaternary o- or p-quinonmethides may be formed intermediarily from the corresponding starting material in which $Y_4$ is free or reactively esterified hydroxy, e.g. under strongly acidic or alkaline conditions, or during the reduction of compounds in which $Y_5$ is oxo or thiono. The α-diazoketones are usually formed, according to Arndt-Eistert, from the corresponding benzoic acid halides and aliphatic or cycloaliphatic ($R_2$) diazo compounds, whereupon the above-described Wolff rearrangement is performed. Moreover, in the formation of the cyclic tert. amino group $A\bigcirc N-$, several intermediates are formed from the various starting materials mentioned above. For example, in the reaction of compounds of Formula IV, in which $X_2$ is primary amino, with those of the formula HO—A—OH or its reactive functional derivatives, usually secondary amines are formed, wherein $X_2$ is —NH—A—OH, or reactive amino derivatives of such intermediates. In the process of the invention, those starting materials are advantageously selected, which yield the above-described preferred embodiments of the invention, especially those corresponding to Formula II.

The starting material used in known or, if new, can be prepared according to the methods described for known analogs thereof, or by the methods illustrated in the examples herein. Thus, compounds of Formula III can be prepared analogous to the process mentioned under item(b), i.e. by introduction or construction of the cyclic amino group $A\bigcirc N-$. In case $X_1$ is a reactively esterified hydroxy group, it may also be introduced either by halogenation, or nitration followed by reduction, diazotization and Sandmeyer reaction. The resulting starting material may be subsequently converted into the metallic compounds, e.g. by reaction with alkali or alkaline earth metals, such as lithium or magnesium, or with dialkyl zinc or cadmium. The allyl ethers for Claisen rearrangement can be prepared analogous to those described in J. Chem. Soc. 4210 (1963).

The starting material in which $Y_2$ is a metallic group may be prepared as shown above, i.e. by reacting reactive esters of the corresponding benzylalcohols with alkali or alkaline earth metals or dialkyl zinc or cadmium. Otherwise, according to Friedel-Crafts, easily obtainable linear or cyclic alkano- or alkenophenones $A\!\!\!\frown\!\!\!N$—Ph—CO—$R_2$ may be reduced either with lithium aluminum hydride or with $R_1$-magnesium halides, or $A\!\!\!\frown\!\!\!N$-Ph-Grignard compounds reacted with $R_1$—CO—$R_2$, to yield the corresponding benzyl alcohols, whose hydroxy group may be reactively esterified or salified according to well-known methods, e.g. by reaction with phosphorus, thionyl or sulfonyl halides, alkali or alkaline earth metals respectively and the resulting esters or salts may be converted into ethers either by reaction with alcoholates or reactive esters respectively. The compounds in which $Y_2$ is an ammonium group, can be obtained from the former reactive esters and secondary amines and the resulting tertiary amines are quaternized in the usual manner, e.g. by reaction with lower alkyl or aralkyl halides.

The starting material containing $Y_3$ can be obtained from the former compounds in which $Y_2$ is a metallic group, by reacting them with a methyl halide, formaldehyde, a formyl halide, lower alkanal, alkenal or hydroxyalkanal or a lower alkanoyl, alkenoyl or oxalyl halide respectively and, if deisred, dehydrating resulting alcohols by the action of acidic agents, e.g. sulfuric acid or phosphorus pentoxide, to yield unsaturated derivatives thereof. The latter, e.g. methylidene compounds, may be reacted with boranes in order to obtain borylmethyl compounds and aldehydes with hydroxylamine, to yield the hydroxyiminomethyl compounds (oximes). The aldehydes, i.e. compounds in which $Y_3$ is formyl, can also be obtained from said ketones $A\!\!\!\frown\!\!\!N$—Ph—CO—$R_2$ by reaction with dimethylsulfoniummethylide or dimethyloxysulfoniummethylide (generated from the corresponding trimethylsulfonium salts) and rearranging the resulting ethyleneoxides to the corresponding aldehydes by the action of Lewis acids, e.g. p-toluene sulfonic acid or boron trifluoride, or according to the Darzens condensation by reacting the above ketones with α-halo-alkanoic or alkenoic acid esters in the presence of alcoholates, e.g. potassium tert. butoxide, saponifying the glycidic esters formed and rearranging and decarboxylating them, advantageously in acidic media, e.g. sulfuric acid.

The starting material containing $Y_4$, which represents free, esterified or etherified hydroxy or mercapto, can be prepared according to the cyanohydrin or analog syntheses, e.g. by reaction of compounds $A\!\!\!\frown\!\!\!N$—Ph—CO—$R_2$ or their thiono analogs, with aqueous potassium cyanide under acidic conditions and, if desired, converting resulting nitriles into other acid derivatives and/or alcohols into corresponding mercapto compounds or reactive esters or ethers thereof, or dehydrating them to unsaturated derivatives. The compounds in which $Y_5$ is oxo or thiono can be obtained according to Friedel-Crafts with the use of suitable $A\!\!\!\frown\!\!\!N$—Ph—H compounds and oxalyl halides. The resulting phenylglyoxylic acid esters may then be reduced with $R_2$-Grignard compounds, if desired, followed by dehydration. Said compounds may also be prepared according to the Ando synthesis by reaction with mesoxalates in the presence of stannic chloride.

The resulting adduct can either by hydrogenated, the malonate formed metallized and reacted with a reactive ester of $R_2$—OH or saponified and decarboxylated. Finally the α-diazoketones are obtained from corresponding benzoic acid halides and $R_2$-diazo compounds and the α-haloketones by halogenating of the corresponding alkanophenones or reacting the former α-diazoketones with hydrohalic acids.

The starting material of Formula IV is prepared analogous to the process mentioned under item (a), by selecting starting materials containing $X_2$ or a group capable of being converted into $X_2$, advantageously nitro, instead of $A\!\!\!\frown\!\!\!N$—. Thus, for example, compounds wherein $X_2$ is mono- or dioxoalkyleneimino, are obtained from those, wherein $X_2$ is amino, by reacting them with lower alkylene ketals of mono- or dioxoalkylene glycols, or preferably reactive esters thereof, e.g. the halides or tosylates mentioned above, and cleaving the ketals obtained with diluted acids. Moreover, said oxo-compounds can be obtained by Dieckmann condensation of compounds of Formula IV, wherein $X_2$ is bis-(lower carbalkoxyalkyl)-amino, preferably in the presence of strong bases, e.g. alkali metal lower alkoxides, following saponification and decarboxylation of the condensation product, e.g. with aqueous alkali metal hydroxides and following pyrolysis respectively. Said oxocompounds can also be converted into corresponding sulfonyl-hydrazones or metal salts thereof and these subjected to pyrolysis, in order to obtain compounds of Formula IV, wherein $X_2$ is olefinic alkenyleneimino.

The pharmacologically active compounds of the invention are useful in the manufacture of pharmaceutical compositions containing an effective amount thereof in conjunction or admixture with excipients suitable for either enteral, parenteral or topical application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, enzymes of the binders or effervescent mixtures and/or (e) adsorbents, colorants, flavors and sweeteners. Injectable compositions are preferably aqueous isotonic solutions or suspensions, and suppositories or ointments are advantageously fatty emulsions or suspensions. They may be sterilized and/or contain adjuvants, such as preserving stabilizing, wetting or emulsifying agents, solution promoters, salts for regulating the osmotic pressure and/or buffers. Said pharmaceutical compositions may also contain other therapeutically valuable substances. They are prepared according to conventional mixing, granulating or coating methods respectively and contain about 0.1 to 75%, preferably about 1 to 50% of the active ingredient.

The following examples are intended to illustrate the invention and are not to be construed as being limitations thereon. Temperatures are given in degrees Centigrade, and all parts wherever given are parts by weight.

EXAMPLE 1

The mixture of 100 g of 4-(3 hydroxypiperidino)-acetophenone, 300 ml of morpholine, 25 g of sulfur and 2 g p-toluene sulfonic acid is refluxed overnight while stirring. It is concentrated under reduced pressure to about half of its original volume, the concentrate cooled and poured into 500 ml of methanol. The mixture is kept overnight in the refrigerator, filtered and the residue recrystallized from methanol, to yield the [4-(3-hydroxypiperidino)-phenyl]-thioacetmorpholid.

The mixture of 100 g thereof and 500 ml of 25% potassium hydroxide in ethylene glycol-water (1:2) is refluxed until homogeneous. It is filtered, the filtrate washed with diethyl ether, the aqueous solution acidified with 2N hydrochloric acid and again washed with diethyl ether. To the aqueous layer di-potassium hydrogen phosphate is slowly added until the pH is 4.5 and the whole is extracted with diethyl ether. The extract is dried, concentrated, and the concentrate diluted with petroleum ether, to yield the [4-(3-hydroxypiperidino)-phenyl]-acetic acid of the formula

I.R. bands at 1720 and 3634 cm$^{-1}$.

The starting material is prepared as follows: The mixture of 100 g of 4-fluoroacetophenone, 150 g of 3-hydroxypiperidine and 250 ml of dimethylsulfoxide is heated on the steam bath for 30 hours. The resulting solution is poured onto ice and the mixture extracted with diethyl ether. The extract is dried, filtered and evaporated, to yield the 4-(3-hydroxypiperidino)-acetophenone, m.p. 93°–95°.

In the analogous manner the 4-(4-hydroxypiperidino)acetophenone (m.p. 125°–127°) is converted into the [4-(4-hydroxypiperidino)-phenyl]-acetic acid of the formula

EXAMPLE 2

The ethyl 3- or 4-(pyrrolino, 2-pentenyleneimino or 3-hexenyleneimino)-phenylacetate or -α-phenylpropionate, or the corresponding 4- or 3-chloro derivatives thereof, are epoxidized in the amino portion with the use of an equivalent amount of perbenzoic acid in chloroform or benzene, at 0°–25°. The mixture is evaporated in vacuo, the residue taken up in water, the mixture extracted with diethyl ether, the extract washed with aqueous sodium bicarbonate, dried and evaporated, to yield the corresponding epoxides. The latter are converted to the corresponding dihydroxy compounds by treatment with aqueous sodium hydroxide, which simultaneously saponifies the ester. The aqueous solution is washed with diethyl ether, adjusted with hydrochloric acid to pH of about 5 and extracted with diethyl ether. The extract is dried, filtered and evaporated, to yield the corresponding hydroxylated acids, for example, the α-[4-(3,4-dihydroxy-pyrrolidino)-phenyl]-acetic or -propionic acid or the α-[3-chloro-4-(3,4-dihydroxy-piperidino)-phenyl]-acetic or -propionic acid.

The starting material is prepared as follows: The mixture of 10.8 g ethyl 4-amino-phenylacetate hydrochloride, 32.4 g 1,4-dibromo-2-butene, 84 g sodium bicarbonate and 500 ml dimethylformamide is refluxed for 6 hours while stirring, filtered hot and the filtrate evaporated in vacuo, to yield the ethyl (4-pyrrolinophenyl)-acetate.

To the stirred mixture of 5.5 g ethyl 4-pyrrolinophenylacetate, 100 ml dimethylformamide and 100 ml toluene, 1.25 g 54% sodium hydride in mineral oil are added portionwise and stirring is continued for 1½ hours at room temperature. Hereupon the solution of 6.8 g methyl iodide in 25 ml toluene is added dropwise during 20 minutes and the mixture is stirred overnight at room temperature. It is filtered and the filtrate evaporated in vacuo, to yield the ethyl α-(4-pyrrolinophenyl)-propionate.

By replacing the methyl iodide by an equivalent amount of ethyl iodide, allyl bromide, 3-cyclopentenyl bromide or cyclopropylmethyl bromide, the ethyl α-(4-pyrrolinophenyl)-(butyrate, 4-pentenoate, α-3-cyclopentenylacetate or α-cyclopropylmethylacetate) are obtained.

Moreover, the 4-fluoro-phenyl-acetonitrile can be reacted with 4-oxo-piperidine, to yield the 4-(4-oxo-piperidino)-phenylacetonitrile, which is hydrolyzed to the free acid and the acid esterified, to yield corresponding ethyl esters. The carbonyl group therein is reduced with one equivalent of Grignard compounds, e.g. methyl-, ethyl- or n-propyl-magnesium bromide, to yield the ethyl 4-[4-hydroxy-4-(methyl, ethyl or n-propyl)-piperidino]-phenyl acetate. Analogously, the α-[3-chloro-4-(4-hydroxy-4-methyl-piperidino)-phenyl]-propionate is obtained.

The 2-pentenyleneimino starting material is prepared as follows: The mixture of 89.6 g ethyl 4-aminophenylacetate, 400 g ethyl acrylate and 100 ml acetic acid is refluxed for 19 hours and concentrated in vacuo. The concentrate is poured onto 500 ml ice water, the mixture made basic with aqueous sodium hydroxide and extracted with diethyl ether. The extract is dried, filtered, evaported, the residue distilled and the fraction boiling at 211°–213°/0.6 mm Hg collected, to yield the ethyl 4-(bis-carbethoxyethylamino)-phenylacetate.

To the solution of 38 g thereof in 100 ml ethanol, that obtained from 3.4 g sodium and 100 ml ethanol is added dropwise and the mixture refluxed for 7 hours. It is evaporated in vacuo, the residue taken up in water, the mixture extracted with diethyl ether, the extract dried, filtered and evaporated, to yield the ethyl 4-(3-carbethoxy-4-oxopiperidino)-phenylacetate.

The mixture of 30.5 g thereof and 300 ml 50% sodium hydroxide is heated at the steam cone for 12 hours. It is cooled, acidified with concentrated hydrochloric acid and the mixture heated for 6 hours. It is evaporated in vacuo, the residue taken up in ethanolic hydrogen chloride, the mixture evaporated again, the residue taken up in water, the mixture made basic with aqueous sodium hydroxide, extracted with diethyl ether, the extract dried and evaporated, to yield the ethyl 4-(4-oxopiperidino)-phenylacetate.

The mixture of 5.2 g thereof, 2.1 g 4-p-toluenesulfonylhydrazide, 3 ml glacial acetic acid and 50 ml ethanol is refluxed for 30 minutes. It is cooled, the precipitate formed filtered off and taken up in the minimum amount of tetrahydrofuran. To the solution, 13 ml 1.6N n-butyl lithium are added dropwise while still under nitrogen at 0–5°. After 30 minutes, the mixture is evaporated at a temperature below 35°, to yield the lithium salt of the ethyl 4-(4-oxopiperidino)-phenylacetate-N-p-toluenesulfonylhydrazone.

3 g thereof are slowly heated first to about 30°–40° and 0.3 mm Hg to effect final drying, and then to 80°–135° for 45 minutes. The residue is taken up in the minimum amount of ethanol, the solution poured on a small column with silica gel and eluted with benzene. The first eluate obtained is evaporated, to yield the ethyl 4-piperideino-phenyl acetate of the formula

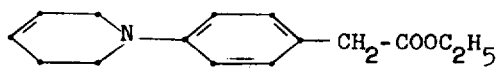

showing in the I.R. spectrum bands at 5.86 and 6.08 μ.

EXAMPLE 3

The mixture of 75 g 4-(4-hydroxypiperidino)-phenyl-thioacetmorpholide and 300 ml 25% aqueous potassium hydroxide is refluxed for 10 hours and allowed to stand in the cold overnight. The precipitate formed is filtered off and recrystallized from ethanol, to yield the sodium 4-(4-hydroxypiperidino)-phenylacetate of the formula

melting at 261°–264°.

The starting material is prepared as follows: The mixture of 100 g 4-(4-hydroxypiperidino)-acetophenone, 300 ml morpholine, 20 g sulfur and 1 g p-toluene sulfonic acid refluxed for 5 hours while stirring and allowed to stand overnight at room temperature. It is diluted with an equal volume of methanol, the mixture cooled, filtered and the residue recrystallized from methanol, to yield the 4-(4-hydroxypiperidino)-phenylthioacetmorpholide melting at 170°–172°.

EXAMPLE 4

The solution of 40 g sodium 4-(4-hydroxypiperidino)phenylacetate in the minimum amount of water is acidified to pH 5 with hydrochloric acid and evaporated in vacuo. The residue is taken up in 200 ml ethanolic hydrogen chloride, the mixture refluxed for 12 hours and evaporated in vacuo. The residue is combined with 150 ml acetic anhydride and the mixture heated at the steam cone for 2½ hours. It is filtered, the filtrate evaporated in vacuo, the residue distilled and the fraction boiling at 149°/0.085 mm Hg collected, to yield the ethyl 4-(4-acetoxypiperidino)-phenylacetate of the formula

EXAMPLE 5

The solution of 13.7 g ethyl 4-(4-acetoxypiperidino)-phenylacetate in 40 ml diethyl ether is added dropwise during 35 minutes to the gray mixture obtained from 1.2 g sodium, 1 crystal ferric nitrate nonahydrate and 700 ml liquid ammonia. After stirring for 1½ hours, the solution of 7.42 g methyl iodide in 25 ml diethyl ether is added during one-half hour and the mixture stirred for an additional hour. Hereupon 5 g ammonium chloride are added, the ammonia allowed to evaporate, the residue taken up in water and the mixture is extracted with diethyl ether. The extract is washed with water, dried, filtered, evaporated in vacuo, the residue distilled and the fraction boiling at 130°/0.1 mm Hg collected, to yield the ethyl α-[4-(4-acetoxypiperidino)-phenyl]-propionate of the formula

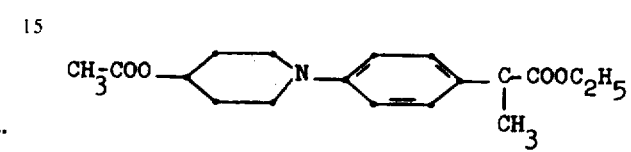

EXAMPLE 6

By replacing in the previous examples the ethyl 4-aminophenylacetate by the corresponding 3-(meta)- or α-substituted analogs, the corresponding ethyl α-[3-methyl, methoxy, methylmercapto, chloro or trifluoromethyl-4-(3,4-dihydroxypiperidino or 4-hydroxy- or 4-acetoxy-4-methylpiperidino)-phenyl]-acetates, -propionates or -β-cyclopropylpropionates, or the corresponding acids are obtained.

The various starting materials are prepared similarly and their synthesis is illustrated as follows: 23 g of 50% sodium hydride in mineral oil are washed with hexane and the washings are decanted off. Thereupon 160 ml of dimethylformamide-toluene (1:4) are added followed by 83.6 of diethyl α-methylmalonate in 200 ml of dimethylformamide-toluene (1:4), which solution is added dropwise while stirring under nitrogen and cooling with ice. After stirring for 30 minutes at room temperature, 100 g of 4-chloro-2-trifluoromethyl-nitrobenzene in 100 ml of toluene are added during one hour and the mixture is stirred overnight at room temperature. Thereupon 200 ml of water are slowly added while cooling, the mixture extracted with diethyl ether, the extract evaporated, the residue distilled and the fraction boiling at 210°–230°/0.55 mm Hg collected, to yield the diethyl α-methyl-α-(3-trifluoromethyl-4-nitrophenyl)-malonate. The corresponding 3-(methyl, methoxy and methylmercapto)-analogs are boiling at 110°–120°/0.2 mm Hg, 155°–170°/0.1 mm Hg or 163°–165°/0.08 mm Hg.

The mixture of 90 g of the trifluoromethyl analog, 106.2 g of iron filings, 10.3 g of ammonium chloride, 417 ml of ethanol and 104 ml of water is heated on the steam bath for 2 hours while stirring. It is evaporated under reduced pressure, the residue taken up in 700 ml of benzene, the mixture filtered, the residue washed with 200 ml of chloroform, the combined filtrate dried, evaporated, the residue distilled and the fraction boiling at 164°–170°/0.4 mm Hg collected, to yield the diethyl α-methyl-α-(3-trifluoromethyl-4-aminophenyl)-malonate.

The mixture of 53 g thereof, 25.2 g of potassium hydroxide, 1.5 liters of ethanol and 30 ml of water is refluxed for 4 hours under nitrogen. It is concentrated under reduced pressure, the concentrate diluted with water, washed with diethyl ether and the pH thereof adjusted with hydrochloric acid to 4.2. It is extracted with diethyl ether, the extract dried, evaporated, the residue distilled and the fraction boiling at 187°–197°/0.15 mm Hg collected, to yield the α-(3-trifluoromethyl-4-aminophenyl)propionic acid melting at 73°–75°.

30 G thereof are dissolved in 500 ml of anhydrous ethanol and through the solution hydrogen chloride is bubbled for one-half hour. It is heated on the steam cone for 3 hours, evaporated, the residue distilled and the fraction boiling at 90°–97°/0.06 mm Hg collected, to yield the corresponding ethyl ester.

The mixture of 100 g (4-amino-phenyl)-acetic acid and 200 ml acetanhydride is heated at the steam cone for 15 minutes and evaporated. The residue is stirred with 500 ml hot water until complete dissolution occurs. The solution is cooled and the precipitate formed filtered off, to yield the (4-acetamido-phenyl)acetic acid melting at 168°–170°.

Into the solution of 77 g thereof in 400 ml glacial acetic acid, a slow stream of chlorine is bubbled at 50° until the spot of the starting material has disappeared in the thin layer chromatogram (4 ml chloroform-ethyl acetate 1:1 and 4 drops formic acid). The mixture is cooled, the precipitate filtered off to yield the crude (3-chloro-4-acetamino-phenyl)-acetic acid.

The mixture of 69 g thereof and 400 ml saturated ethanolic hydrochloric acid is refluxed for 3 hours and cooled. The precipitate formed is filtered off and washed with ethanol to yield the ethyl (3-chloro-4-amino-phenyl)-acetate hydrochloride melting at 167°–168°.

To the solution of 10 g ethyl 4-nitrophenylacetate in 400 ml dimethyl formamide-toluene (1:1), 2.5 g 50% sodium hydride are added portionwise during 15 minutes while stirring and cooling with ice, after which the solution of 9.6 g cyclopropylmethyl bromide in 50 ml toluene is added dropwise and the mixture stirred overnight at room temperature. It is diluted with 200 ml water, extracted with diethyl ether, the extract dried, evaporated, the residue distilled and the fraction boiling at 132°–138°/0.25 mm Hg collected, to yield the ethyl α-(4-nitrophenyl)-β-cyclopropylpropionate.

The solution of 9 g thereof in 100 ml ethanol is hydrogenated over 0.5 g 10% palladium on charcoal until the theoretical amount of hydrogen has been absorbed. The mixture is filtered, the filtrate evaporated in vacuo, the residue taken up in diethyl ether, the solution gassed with hydrogen chloride, the precipitate formed filtered off and recrystallized from ethyl acetate, to yield the ethyl α-(4-aminophenyl)-β-cyclopropylpropionate hydrochloride melting at 160°–162°.

EXAMPLE 7

Preparation of 10,000 tablets each containing 20.0 mg of the active ingredient:

Formula

| | |
|---|---|
| Sodium 4-(4-hydroxy-piperidino)-phenyl-acetate | 200.00 g |
| Lactose | 1,057.00 g |
| Corn starch | 75.00 g |
| Polyethylene glycol 6,000 | 75.00 g |
| Talcum powder | 75.00 g |
| Magnesium stearate | 18.00 g |
| Purified water | q.s. |

Procedure

All the powders are passed through a screen with openings of 0.6 mm. Then the drug substance, lactose, talcum, magnesium stearate and half of the starch are mixed in a suitable mixer. The other half of the starch is suspended in 40 ml water and the suspension added to the boiling solution of the polyethylene glycol in 150 ml water. The paste formed is added to the powders which are granulated, if necessary, with an additional amount of water. The granulate is dried overnight at 35°, broken on a screen with 1.2 mm openings and compressed into tablets using concave punches with 6.4 mm diameter, uppers bisected.

In the analogous manner tablets can be prepared, containing the same amount of another preferred drug substance, e.g. such corresponding to Formula II.

EXAMPLE 8

To the solution of 2.0 g of α-(4-amino-3-chlorophenyl)propionic acid in 20 ml of ethanol, 1.4 g of 1,4-dichloro-2-butanol are added, followed by 4 g of potassium carbonate while stirring. The mixture is stirred for 4 hours at the steam cone and evaporated under reduced pressure. The residue is taken up in water, the solution acidified with N hydrochloric acid to a pH of 5.5 and extracted with diethyl ether. The extract is dried, filtered and evaporated, to yield the α-[3-chloro-4-(3-hydroxypyrrolidino)-phenyl]-propionic acid of the formula

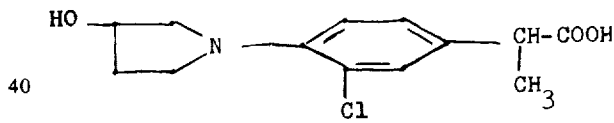

showing in the I.R. spectrum bands at 1718 and 3640cm⁻¹.

EXAMPLE 9

The solution of 0.5 g of α-[3-chloro-4-(3,4-oxidopyrrolidino)-phenyl]-propionic acid in 5 ml of 2N aqueous sodium hydroxide is heated at the steam bath for 2½ hours. It is cooled, the pH of the solution adjusted to 5 with hydrochloric acid and the mixture extracted with diethyl ether. The extract is dried evaporated, the residue chromatographed on silica gel and the column eluted with 100 ml of methanol-diethyl ether (1:9). The last third of the eluate is evaporated, to yield the α-[3-chloro-4-(trans-3,4-dihydroxypyrrolidino)-phenyl]-propionic acid of the formula

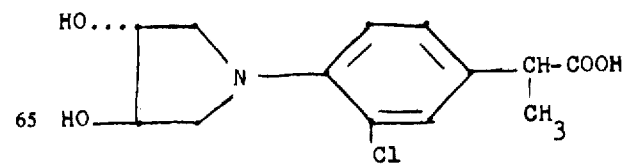

showing in the I.R.-spectrum bands at 1200, 1600, 1725 and 3350cm$^{-1}$.

The starting material is prepared as follows: To the solution of 2.6 g of methyl α-(3-chloro-4-pyrrolinophenyl)-propionate in 50 ml of methanol, the mixture of 3.5 g of acetonitrile, 4 ml of 30% aqueous hydrogen peroxide and 1 g of potassium bicarbonate is added and the resulting solution stirred for 2.5 hours at room temperature. It is evaporated under reduced pressure, the residue taken up in 10 ml of water and the mixture extracted with diethyl ether. The extract is dried, evaporated and the residue chromatographed on silica gel. The column is first eluted with benzene, followed by ethyl acetate and the latter eluate evaporated. The residue is taken up in 3 ml of 30% aqueous potassium hydroxide and 40 ml of methanol, the solution stirred at room temperature for 2 hours and evaporated. The residue is taken up in water, the pH of the solution adjusted to 5 with hydrochloric acid and the mixture extracted with diethyl ether. The extract is dried, evaporated and the residue triturated with cyclohexane, to yield the α-[3-chloro-4-(3,4-oxidopyrrolidino)-phenyl]-propionic acid, melting at 94° to 96°.

EXAMPLE 10

To the solution of 1.0 g of α-(3-chloro-4-pyrrolinophenyl)-propionic acid in 20 ml of diethyl ether and 0.4 ml of pyridine, that of 1.0 g of osmium tetroxide in 20 ml of diethyl ether is added during 30 minutes while stirring and cooling with ice. After stirring for another 30 minutes at 0°, the mixture is filtered and the precipitate washed with diethyl ether. It is added to the solution of 10 g of sodium sulfite heptahydrate, 40 ml of water and 25 ml of ethanol, the mixture stirred and refluxed for 3 hours and stirred overnight at room temperature. It is filtered, the precipitate washed with ethanol and the filtrate concentrated to 30 ml under reduced pressure. The pH of the concentrate is adjusted with hydrochloric acid to 3.5 and the mixture extracted with ethyl acetate. The extract is dried, evaporated and the residue recrystallized from diethyl ether with the acid of charcoal, to yield the α-[3-chloro-4-(cis-3,4-dihydroxypyrrolidino)-phenyl]propionic acid melting at 112°-114°.

We claim:
1. A compound of the formula

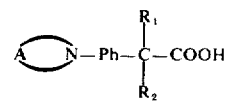

in which $R_1$ is hydrogen, $R_2$ is hydrogen, lower alkyl or 3 to 7 ring-membered cycloalkyl, Ph is 1,3- or 1,4-phenylene, (lower alkyl)-1,3- or 1,4-phenylene, (lower alkoxy)-1,3- or 1,4-phenylene, mono- or di-(halogeno)-1,3- or 1,4-phenylene, (trifluoromethyl)-1,3- or 1,4-phenylene, or (di-lower alkylamino)-1,3- or 1,4-phenylene, the group A⟩N— is 5 to 8 ring-membered hydroxyalkyleneimino, wherein the oxygen atom is separated from the nitrogen atom by at least two carbon atoms, or a lower alkyl ester, the amide, an alkali metal or alkaline earth metal salt or a therapeutically useful acid addition salt thereof.

2. A compound as claimed in claim 1 and being [4-(3-hydroxypiperidino)-phenyl]-acetic acid.

3. A compound as claimed in claim 1 and being [4-(4-hydroxypiperidino)-phenyl]-acetic acid.

4. A compound as claimed in claim 1 and being ethyl 4-[4-hydroxy-4-(methyl or ethyl)-piperidino]-phenyl acetate.

5. A compound as claimed in claim 1 and being ethyl α-[3-chloro-4-(4-hydroxy-4-methyl-piperidino)-phenyl]-propionate.

* * * * *